United States Patent [19]
Lasky

[11] Patent Number: 4,618,973
[45] Date of Patent: Oct. 21, 1986

[54] MAMMOGRAPHIC X-RAY APPARATUS
[76] Inventor: Harold J. Lasky, 716 Roslyn Pl., Evanston, Ill. 60201
[21] Appl. No.: 794,048
[22] Filed: Nov. 1, 1985
[51] Int. Cl.⁴ .......................... A61B 6/04; G03B 41/16
[52] U.S. Cl. .................................... 378/037; 378/180; 378/195
[58] Field of Search ................. 378/37, 208, 209, 295, 378/180; 250/515.1

[56] References Cited
U.S. PATENT DOCUMENTS

| | | | |
|---|---|---|---|
| 3,556,081 | 1/1971 | Jones | 378/037 |
| 3,578,971 | 5/1971 | Lasky | 378/037 |
| 3,973,126 | 8/1976 | Redington et al. | 378/037 |
| 4,051,380 | 9/1977 | Lasky | 378/037 |

Primary Examiner—Craig E. Church
Assistant Examiner—T. N. Grigsby
Attorney, Agent, or Firm—Trexler, Bushnell & Wolters, Ltd.

[57] ABSTRACT

In combination with an apparatus for conducting radiographic examination of the breast under tissue compressive conditions, a positionably adjustable table serving as a support for body components and as a shield against radiation exposure during operation of X-ray equipment in carrying-out the method of the invention. There is also disclosed an improved mechanism for controllably positioning the compressive plates between which the breast of the patient is restrained during radiographic examination.

10 Claims, 8 Drawing Figures

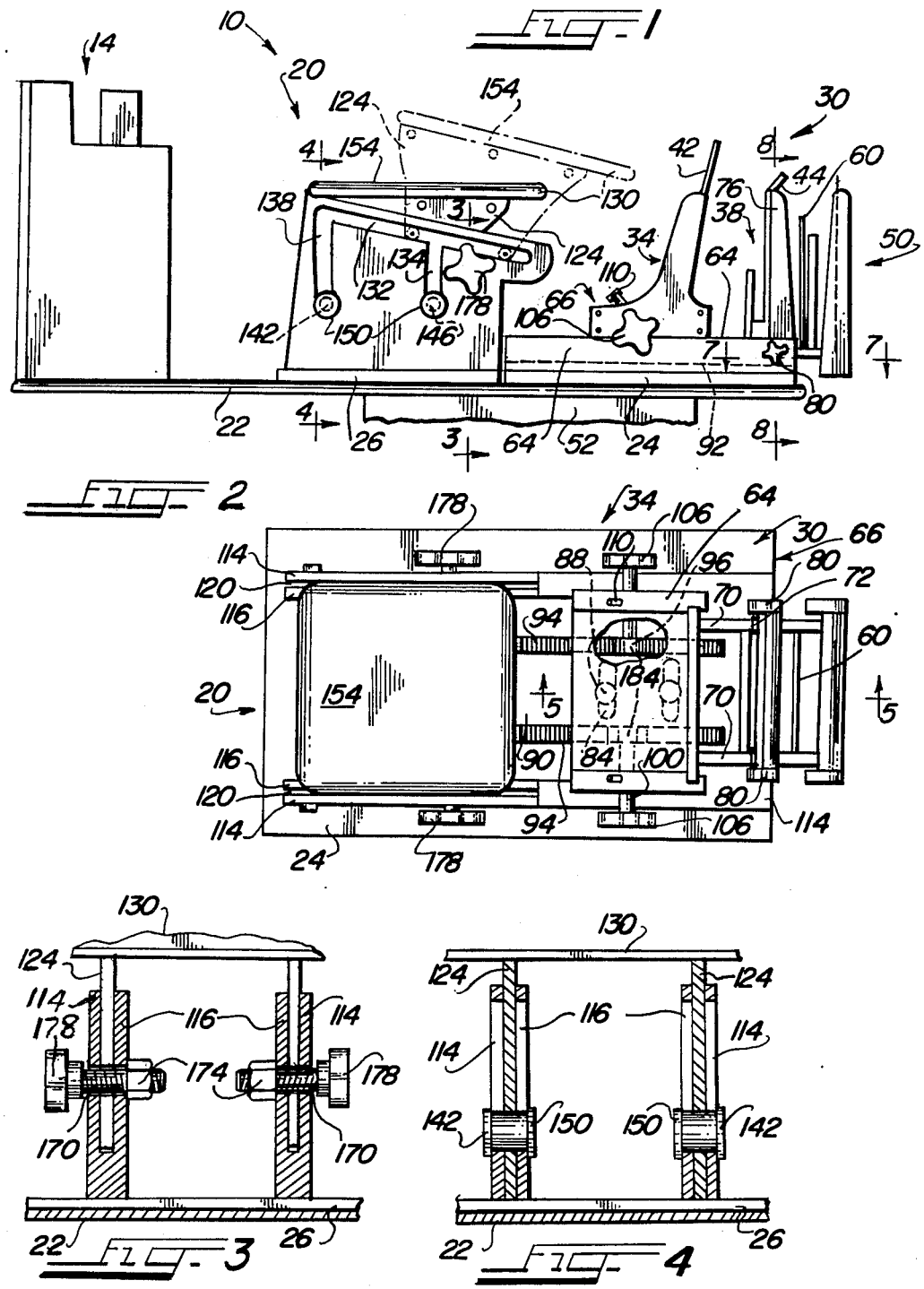

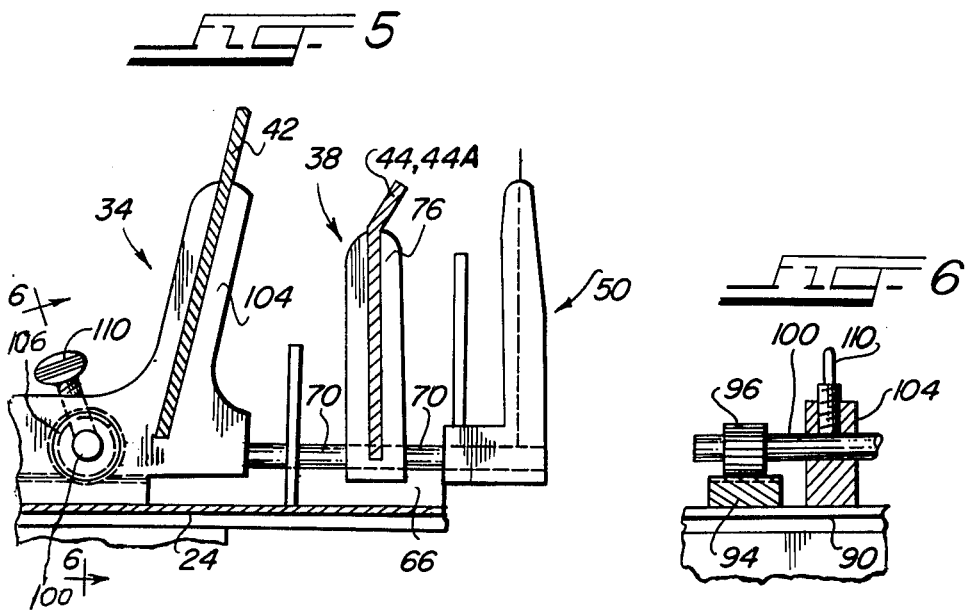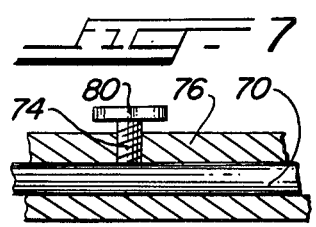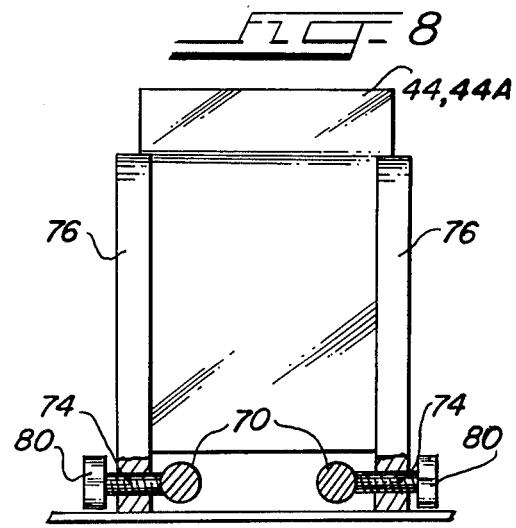

MAMMOGRAPHIC X-RAY APPARATUS

BACKGROUND OF THE INVENTION

This invention relates to apparatus and methods for medical radiographic examination. More particularly, the invention is directed to auxiliary apparatus used in enhancing the mode of conducting diagnostic X-ray examination and for detecting internal growths including tumors, cancer and other types of defects and abnormalities in the female breast.

The general method employed in the subject invention includes gravitationally suspending the breast between compressive plates during radiographic exposure. The technique itself and the basic apparatus for carrying-out the method are described in Lasky U.S. Pat. No. 3,578,971, and the entire disclosure of that patent is hereby specifically incorporated herein by reference to the extent it is not inconsistent herewith.

Radiographic or X-ray examination techniques have been widely employed in the past for the medical diagnosis and the detection of tumorous body growths. The instant application is directed specifically to mammography, the technique broadly used in the detection of breast tumors, cancer, and other growths in the adult female breast.

The present invention invokes the teachings of the above-identified Lasky U.S. Pat. No. 3,578,971 and provides auxiliary apparatus enhancing the technique and further obviating the shortcomings and deficiencies of prior art procedures. As in the reference referred to, the present invention utilizes the technique of examining the breast under conditions such that internal structures are radiographically displayed for diagnostic visualization, in their most orderly anatomic arrangement and under conditions of reduced and substantially uniform tissue thickness to permit minimal radiation exposure and to ensure optimum field of examination, sharp image focus, and even image density.

SUMMARY OF THE INVENTION

The present invention utilizes the technique of gently yet firmly compressing the breast of a female subject while the breast is gravitationally suspended, and carrying-out the radiographic examination under the conditions described.

It is an important feature of the present invention that it provides a simple yet highly effective apparatus to facilitate carrying-out the technique which combines gravitational suspension with controlled compression of tissue.

A related feature of the invention is that it provides improved means for quickly and conveniently adjusting the spacing of compression wall means of the apparatus of the invention so that the wall spacing or separation is correlated with an elected, professionally-determined, degree of controlled compression of the breast gravitationally suspended in a channel extending between the wall means, during X-ray exposure of the breast.

Yet another important structural feature of the present invention, aiding in the conduct of the method of the invention, is the provision of an auxiliary table or support which is used, selectively, as a rest for either the patient's head or for a breast of the patient, depending upon the particular "view" that is involved in the specific radiographic exposure being conducted.

Yet another object of the invention is to provide improved means for quickly and conveniently adjusting the spacing of the wall means of the apparatus of the invention so that the wall spacing or separation is effectively correlated with an elected, professionally-determined, degree of controlled compression of the breast gravitationally suspended in a channel extending between the wall means, during X-ray exposure of the breast.

It is an important feature of the invention that there is provided an adjustable table or support which serves the dual function of supporting a body component during the X-ray examination and, concurrently, protecting that body component from exposure to radiation from the X-ray source.

A related feature of the invention is that the novel shielding and support table is rendered adjustable to assume a preferred spacial location and mode to accommodate the body component for which it serves as a protective rest.

Yet another feature of the invention is that there is provided a simple yet highly effective drive mechanism by which the relative spacing of the tissue compressing walls is adjusted to the desired value correlated with the professionally dictated degree of compression desired.

Other and further objects, features, and advantages of the invention will become apparent from a consideration of the following specification taken in conjunction with the drawings.

BRIEF DESCRIPTION OF THE DRAWINGS

The following drawings, in which like components and parts are designated by like numerals, provide a means for enhancing the understanding of the invention as described more fully in the specification set forth below.

FIG. 1 is a side elevational view of the mammographic X-ray apparatus of the invention, including the tissue restraining elements as well as the X-ray radiation source;

FIG. 2 is a top plan view of the mammographic apparatus of FIG. 1;

FIG. 3 is a cross-sectional view taken substantially on the line 3—3 of FIG. 1, and showing the table-locking clamp mechanism;

FIG. 4 is a cross-sectional view taken substantially on the line 4—4 of FIG. 1 and showing one of the slide slots for vertical positioning of the table of the invention;

FIG. 5 is a cross-sectional view taken substantially on the line 5—5 of FIG. 2 and showing the relationship between the pressure applying plates and the film holder of the apparatus of the invention;

FIG. 6 is a cross-sectional view taken substantially on the line 6—6 of FIG. 5 and showing the mechanism for locking the front, sliding plate assembly in place;

FIG. 7 is a cross-sectional view taken substantially on the line 7—7 of FIG. 1 and showing the securement screw for locking the rear plate support assembly in place; and FIG. 8 is a cross-sectional view taken substantially on the line 8—8 of FIG. 1 and showing the rear plate support assembly in elevation and a cross-sectional view of the plate locking mechanism.

DETAILED DESCRIPTION OF PREFERRED EMBODIMENTS

The aims and objects of the invention are realized by providing an auxiliary table or platform which serves the dual function of a body component rest and a protective shield to prevent irradiation of the body component during radiographic examination of tissue restrained between compressive wall elements of the device of the invention. That examination is carried out while the breast of the patient is gravitationally suspended and while the breast is, concurrently, compressed, thus ensuring an orderly anatomic arrangement and a more uniform tissue thickness. The examination is conducted utilizing conventional X-ray equipment in conjunction with the improved mechanical accessories of the invention, a preferred embodiment of which is illustrated in the drawings and described more fully herebelow.

Referring now to the drawings, and particularly to FIG. 1, the device 10 of the invention includes an X-ray source 14, an adjustable rest or support which also functions as an X-ray shield 20, a table top 22, base plates 24 and 26, an assembly 30 which includes a pair of frames 34 and 38 including means for adjusting the relative spacing therebetween, the frames 34 and 38 carrying tissue-embracing elements 42 and 44 or 44A. The latter element may be either a plastic sheet 44 or an X-ray shield 44A, depending upon the particular view being taken. A selectively removable film holder 50 is carried at the end of the assembly away from the X-ray source. The various components including the radiation source 14, the adjustable body support assembly 20 and the tissue restraining elements 34 and 38 are conveniently carried on and secured to a wheeled cart 52.

The longitudinally shiftable wall support frame 34 and the fixed frame 38 each carry tissue compressing elements which constitute plastic sheets or panels 42 and 44 of polyalkyl acrylate (Lucite or Plexiglas) or of a polycarbonate (Lexan). The plastic walls 42 and 44 themselves are radiation transparent and define therebetween the radiation chamber in which the breast is gravitationally suspended while the walls engage and compress the tissue during radiographic examination.

An X-ray sensitive material 60, in a paper holder or other suitable container is placed either within (in a direction toward the X-ray source 14) the rearwardly disposed wall 44A in which case the wall 44A is a radiation shield. Exposure then takes place through a single plastic sheet 42. Alternatively, the X-ray sensitive material is positioned outside the rearwardly disposed wall 44 in which event the wall element 44 is a plastic sheet, and exposure is made through two plastic sheets 42 and 44. The spacial separation between the two walls 42 and 44 (or 44A) is then adjusted by shifting the assembly 34 along support rails 64 of the frame carrying base 66 toward the fixed assembly 38 to compress the breast tissue between the two walls 42 and 44 (or 44A).

With the walls 42 and the opposed wall 44 (or 44A) locked in position, the radiographic material 60 is exposed, either through the forward plastic sheet 42 by a horizontally projected X-ray beam emanating from the X-ray source 14, or through two plastic sheets 42 and 44. The exact arrangement depends upon the placement of the radiation shield, the placement position being dictated by the particular projection being made. For example, when the patient is in a position for making a cephalocaudal projection, an X-ray impermeable backing or shield 44A is mounted in place of the plastic sheet 44 in assembly 38. The X-ray film or sensitive material 60 for this view is positioned between the radiation shield 44A and the breast, and is in contact with the breast itself. In taking the lateral view, the breast is between the plastic sheets 42 and 44.

In the particular preferred embodiment of the invention illustrated, the forward frame 34 may be shifted forwardly and rearwardly with respect to the fixed frame 38 so as to accommodate the breast between the restraining walls 42 and 44. In the example of the invention illustrated, the rearwardly positioned assembly 50 includes a forwardly projecting pair of laterally spaced slide bars, rods or guides 70 passing through bushings 72 carried by the base 66. The assembly 50 is selectively positionable forwardly and rearwardly and is locked in place by means of a probe-like pin 74 (FIG. 8) threaded into and extending through the side wall 76 of the frame 38 stressingly to abut and bear against the slide bar 70. Actuation of the threaded pin 74 is by means of a hand crank 80, all as shown in FIGS. 1, 2, 7 and 8.

As indicated schematically in FIG. 2 the assembly 30 is shiftable laterally along transverse slots 84, threaded locking bolts 88 being provided to secure the assembly in place. The forward frame 34 is positionably supported on the rails 64 surmounting a floor 90 of the assembly 30. Secured to the floor 90 of the assembly 10 are a pair of laterally spaced longitudinally extending ratchet bars 94 (FIG. 2). These meshingly engage a pair of cooperating gears 96 carried on a horizontally extending shaft 100, the latter passing through opposed framing elements 104 and provided, at each of the opposed ends of the shaft 100, with a hand crank 106 (FIG. 5) by means of which the gears 96 are caused to rotate thereby to move the shiftable frame 34 forwardly or rearwardly, as desired. Adjustable frictional resistance to the movement of the frame 34 is conveniently achieved by means of a thumb screw 110 threaded in the frame wall 104 and turnable positively to engage and stressingly to bear against the shaft 100, as indicated schematically in FIGS. 5 and 6.

An important feature of the present invention is a support table assembly 20 which, as shown in FIGS. 1 and 2, is located between the radiation source 14 and the tissue compressing wall support frames 34 and 38. The table assembly 20 includes a pair of laterally spaced supports each constituting a pair of spaced walls 114 and 116 (FIG. 3) defining a vertical slot 120 (FIG. 2) which slidably receives therewithin each of the corresponding side walls 124 which support the table top 130. As best seen in FIG. 1, the walls 114 and 116 are formed with transverse through slots each defining a generally upwardly angled principal slot 132 communicating with intersecting rearward and forward slots 134 and 138. The latter extend generally vertically and intersect the principal slot 132 respectively at a mid position and at a forward extremity (FIG. 1).

The walls 124 of the table itself are provided with stud shafts or bosses 142 and 146 which extend transversely through the table walls 124 and through the slots in the base walls 114 and 116, the stub shafts 142 and 146 being capped, headed, or otherwise provided with means 150 which preclude lateral displacement from the assembly. Thus, the shafts 142 and 146 and their associated caps 150 lock the table assembly 20 to the base walls 114 and 116 so as to restrict movement of the table 130 to follow paths delineated by the slots 132, 134 and 138.

The table 130 may be slidably positioned forwardly and rearwardly at any selectable location along the upper slot 132. Specifically, the table 130 may be slid forwardly along the slot 132 so that the stub shafts 142 and 146 align respectively with the vertical slots 138 and 134, whereupon the table may be moved to its lower or depressed position. The arrangement described delineates optional positions of placement and orientation of the table and, accordingly, the disposition and location of the table top 130 or rest surface 154 itself.

In the arrangement described, the table walls 124 are readily and easily slidable within the sandwiching or embracing walls 114 and 116, to selectable positions, and permit orientation dictated and limited by the arrangement of the slots 132, 134 and 138. While any preferred mechanism may be utilized for securing the table in a specific selected position, in the particular embodiment of the invention illustrated, the method of securement is by means of a pair of threaded bolts 170 (FIG. 3) which extend through the slot-defining walls 114 and 116. Locking nuts 174 are secured on the ends of the bolts 170 interiorly of the apparatus, and at their outer ends the bolts are capped by interiorly threaded hand cranks 178. It will be readily appreciated that upon tightening of the hand cranks 178 onto the bolts 170, the spaced walls 114 and 116 are urged toward each other and stressingly sandwich and positively engage and lock against the table side walls 124 so as fixedly to secure the table top 130 in place.

The manner in which the apparatus of the invention, particularly the novel table support assembly 20, is used will be described below with reference to FIGS. 1 and 2. The apparatus 10 is carried upon and is conveniently supported on the top of an X-ray cart 52 and need not be moved for any view. For the cephalocaudal view the patient stands at the foot of the table, facing the X-ray tube 14, bends forwardly over the frame 38 and wall 44A, suspends the breast between the walls 42 and 44A, and rests her head on the top surface 154 of the table 130. The table top 130 itself is, at this time, in its lowered or depressed mode so that the supporting shafts 142 and 146 lie at the bottom of the slots 134 and 138. In this arrangement, the patient's head rests on the platform or table top 130 and, with compression applied by ratcheting the frame 34 toward the frame 38, the exposure is made. For this view, assembly 50 is removed from the apparatus, the X-ray shield 44A is in place, the X-ray sensitive material 60 is between the compressed breast and the shield 44A.

For the lateral view, the patient stands at the side of the apparatus-supporting cart 52 and bends forwardly and suspends the breast between the plastic panels 42 and 44. In this position the opposite breast and chest are supported by the elevated table top 130 (the support shafts 142 and 146 being then within the slots 132). For this view, assembly 50 is in place, the X-ray shield (44A) is removed and replaced with a plastic sheet 44 and the X-ray sensitive material 60 is held in position on assembly 50. The X-ray beam then goes through plastic sheet 42, the compressed breast, plastic sheet 44 and then strikes the senstive material 60.

In each of the procedures described above the table assembly 20 serves the dual function of supporting a body component and of shielding that component against exposure to the generated X-ray beam. It will be appreciated that the table top 130 when elevated is adjustable for forward and rearward displacement, thus accommodating the particular requirements for any specific examination procedure being conducted. Upon having been located in the desired position and attitude, the table assembly 20 is locked in place by tightening the hand wheels 178.

The physical components of the apparatus, for carrying out the method of the invention, may be fabricated of any suitable structural materials. It is important, however, that at least one and preferably both of the radiation-chamber-defining walls 42 and 44 be visually transparent so that the positioning of the breast may be readily viewed to ensure proper placement for radiographic display. The frame 38 for the rearward wall 44 is stationary. The opposed frame assembly 34 is conveniently positionable forwardly and rearwardly by means of the combination gear 96 and ratchet 94, by rotation of the gear 96 through the handle 106. When in the position selected, the gear 96 is held in place on the ratchet 94 being frictionally adjusted by a thumb screw assembly 110 which bears against the shaft 100 coupling the handle 106 to the gear 96.

In the preferred embodiment of the invention described, the drive gear 96 includes a flattened "toothless" sector 184 which, when presented to face the ratchet 94 frees the gear from engagement with the ratchet and permits one to slide the movable frame 34 along the support rails 64.

It will be appreciated that in carrying out the wall-shifting and positioning operation, it is necessary that the operator be able to "sense" the degree of resistance to compression so as properly to control the pressure applied.

The improved technique and apparatus of the present invention for breast compression for mammography has been found to be exceedingly simple, fast and accurate and to provide a desirable high degree of reproducability. Motion of the patient is not a problem, and the technique has facilitated the preparation of oblique views which are completely and simply feasible with the apparatus of the invention. It has been established that flattening of the breast enhances penetration of the base.

The technique of the invention requires no special cones or equipment changes and produces uniformly high quality radiographs with minimum patient exposure. Absorption by the intervening plastic panels has posed no-problem; nor has there been any deleterious effect on the image detail.

While the present invention has been described with reference to preferred embodiments and compositions, it will be appreciated that certain changes may be made in the technique and in the apparatus without departing from the scope of the invention, such changes and modifications being within the skill of those familiar with the art and without the requirement of utilizing the inventive faculty. It is intended, accordingly, that all matter contained in the description set forth above and illustrated in the accompanying drawings shall be interpreted as illustrative and not in any limiting sense.

What is claimed is:

1. An apparatus to facilitate the X-ray examination of the breast of a female subject and including:
   a radiation source and means for directing said source to impinge upon target tissue to be examined,
   radiation energy sensor means responsive to radiation emanating from said radiation source and impinging on said sensor means to provide a visual image of said tissue,
   wall means for confining said tissue to be examined and for applying controlled compression force thereto during exposure of said tissue to said radiation source, said means for confining said tissue including spaced wall means disposed positively to engage said tissue gravitationally suspended therebetween, at least one of said wall means comprising a sheet of material transparent to visible light to facilitate viewing of the positioning of the breast to ensure proper placement for radiographic display, means for shifting said wall means relative to each other to establish selectable spacing correlated with associated compression forces applied by said wall means to said tissue to establish a controlled through thickness field of said tissue presented to said radiation source and to provide more uniform density in visual images produced, the improvement comprising:

generally horizontally extending table means interposed intermediate said radiation source and said wall means for supporting a body component of the subject thereon and for shielding said body component from irradiation during radiographic examination of the subject, means for manipulatively positioning said table means in a selectable mode correlated with a particular physical attitude assumed by the subject and dictated by orientation of the tissue being examined, guide means for delineating optional positions of said table means, said guide means including channel means and shaft means slidably disposed in said channel means, said shaft means cooperating with said channel means to delineate optional paths of movement of said table means, means supporting said table means in said guide means, and locking means for securing said table means in said guide means at a selectable positional and angular orientation.

2. The structure as set forth in claim 1 wherein said wall means comprise a pair of spaced, opposed, walls movable relatively toward and away from one another, and positive drive means for controlling displacement of a first said wall means with respect to a second said wall means for establishing a predetermined selectable degree of compression upon target tissue to be examined during confinement between said wall means.

3. The structure as set forth in claim 1 and further comprising a base, and wherein said positive drive means for moving a first of said wall means longitudinally toward and away from a second of said wall means comprise, in combination, intercoupled rack and gear means, one of said rack and gear means being fixed with respect to said base and the other being movable therealong with a first of said wall means, and handle means for rotating said gear means relative to, to travel along said rack means for establishing a selectable spacing between said wall means, said spacing being correlated with a predetermined degree of compression to be impressed upon tissue interposed between said wall means during radiographic examination of the tissue.

4. The structure as set forth in claim 1 wherein said table means includes flange means connected to and extending transversely thereof and projecting therebelow at laterally spaced positions therealong, and wherein said means for manipulatively positioning said table means includes a base, spaced strut means carried by and extending upwardly from said base adjacent opposed sides thereof, cooperating guide means carried by said flange means of said table means and said strut means of said base for facilitating movement of said table means upwardly, downwardly, forwardly, rearwardly, and pivotally for adjustably positioning said table means to assume a selectable mode, and clamping means for locking said table means in said selectable mode.

5. The structure as set forth in claim 4 wherein said cooperating guide means comprise slots in said strut means and transverse shafts carried by said flange means and riding in said slot means.

6. The structure as set forth in claim 5 wherein each of said strut means includes a pair of spaced wall elements for slidably receiving a corresponding said flange means of said table means therebetween, and wherein said clamping means include means for drawing respective said wall elements toward one another grippingly to sandwich corresponding said flange means therebetween to lock said table means in selectable attitudes for functional use.

7. The structure as set forth in claim 2 including first and second walls of said wall means, and further comprising rail means for supporting and for guiding said first wall of said wall means along a lineal course toward and away from said second wall of said wall means, a hand-energized crank, slide bar and rack and gear assembly for selectively positioning said first wall, and pin means carried by said first wall of said wall means and operable stressingly to engage said slide bar frictionally to secure said first wall in selectable spaced positions with respect to said second wall.

8. The structure as set forth in claim 4 wherein said clamping means comprise manually actuatable threaded bolts for urging said strut means of said base into compressive contact with said flange means of said table means rendering said strut means and said flange means immobilized relative to one another.

9. The structure as set forth in claim 1 and further comprising a base plate including frame means supporting said wall means on said base plate, said base plate and said frame means including intercoupled bolting means and transversely disposed cooperating slot means for facilitating physical displacement of said wall means laterally to selectible positions for adjustably confining target tissue to be compressed between said wall means for radiographic examination.

10. The structure as set forth in claim 7 and further comprising a crank-shaft-rotated gear of said assembly for engaging said rack to travel therealong during positioning of said first wall with respect to said second wall, and wherein said gear includes a cut-away, tooth-free annular sector free from intercoupling mechanical interlocking engagement with said rack, said tooth-free sector facilitating sliding manual selective displacement of said first wall of said wall means with respect to said second wall during positional adjustment of said first wall with respect to said second wall.

* * * * *